US010172931B2

(12) United States Patent
Chang et al.

(10) Patent No.: US 10,172,931 B2
(45) Date of Patent: Jan. 8, 2019

(54) BACULOVIRUS DISPLAY VECTORS AND USES THEREOF

(71) Applicant: Reber Genetics Co., Ltd., Taipei (TW)

(72) Inventors: Chia-Jung Chang, Taipei (TW); Yan-Chiou Liao, Taipei (TW); Wei-I Chou, Taipei (TW); Hsiu-Kang Chang, Taipei (TW)

(73) Assignee: REBER GENETICS CO., LTD., Taipei (TW)

( * ) Notice: Subject to any disclaimer, the term of this patent is extended or adjusted under 35 U.S.C. 154(b) by 0 days.

(21) Appl. No.: 15/153,851

(22) Filed: May 13, 2016

(65) Prior Publication Data
US 2016/0331826 A1    Nov. 17, 2016

Related U.S. Application Data

(60) Provisional application No. 62/162,139, filed on May 15, 2015.

(51) Int. Cl.
*C07K 14/005* (2006.01)
*A61K 39/12* (2006.01)

(52) U.S. Cl.
CPC ............ *A61K 39/12* (2013.01); *C07K 14/005* (2013.01); *C07K 2319/02* (2013.01);
(Continued)

(58) Field of Classification Search
None
See application file for complete search history.

(56) References Cited

U.S. PATENT DOCUMENTS

| 7,527,967 B2 | 5/2009 | Chao et al. |
| 7,750,204 B2 * | 7/2010 | Kodama ............ A01K 67/0275 800/18 |

(Continued)

FOREIGN PATENT DOCUMENTS

| WO | WO 0220048 | * 7/2001 | ............. A61K 39/12 |

OTHER PUBLICATIONS

Alexandra Spenger, et. al. "Altering the surface properties of baculovirus Autographa californica NPV by insertional mutagenesis of the envelope protein gp64" Eur J Biochem. Sep. 2002;269(18):4458-67.

(Continued)

*Primary Examiner* — Michelle S Horning
(74) *Attorney, Agent, or Firm* — Hsiu-Ming Saunders; Intellectual Property Connections, Inc.

(57) ABSTRACT

A recombinant baculovirus displaying on its envelop a fusion protein is disclosed. The fusion protein comprises a heterologous antigen, and a C-terminal region of baculovirus envelope GP64 protein, which has at least 100 amino acid residues in length and lacks a B12D5 binding epitope located within the central basic region of the GP64 protein. The genome of the recombinant baculovirus comprises a transgene encoding a fusion protein that comprises a signal peptide, the heterologous antigen, and the C-terminal region of the baculovirus envelope GP64 protein, in which the antigen is located between the signal peptide and the C-terminal region of the GP64 protein. Methods for eliciting an antigen-specific immunogenic response in a subject in need thereof are also disclosed.

17 Claims, 3 Drawing Sheets

Specification includes a Sequence Listing.

(52) U.S. Cl.
CPC ............... *C07K 2319/735* (2013.01); *C12N 2710/14122* (2013.01); *C12N 2710/14143* (2013.01); *C12N 2770/20022* (2013.01); *C12N 2770/20034* (2013.01); *C12N 2770/24322* (2013.01); *C12N 2770/24334* (2013.01)

(56) References Cited

U.S. PATENT DOCUMENTS

2010/0196419 A1\*  8/2010  Compans ............... A61K 39/21
                                                     424/204.1
2011/0201086 A1\*  8/2011  Kawasaki ............. C12N 15/86
                                                     435/235.1

OTHER PUBLICATIONS

Kitidee et al. "Baculovirus display of single chain antibody (scFv) using a novel signal peptide" BMC Biotechnology 2010, 10:80.

Premanand et al. (2013) "Recombinant Baculovirus Associated with Bilosomes as an Oral Vaccine Candidate against HEV71 Infection in Mice" PLoS ONE 8(2): e55536.

Yang et al. "Avian Influenza Virus Hemagglutinin Display on Baculovirus Envelope: Cytoplasmic Domain Affects Virus Properties and Vaccine Potential" Molecular Therapy vol. 15 No. 5, 989-996 May 2007.

Zhou et al. "Mapping the Conformational Epitope of a Neutralizing Antibody (AcV1) Directed Against the AcMNPV GP64 Protein" Virology. Sep. 1, 2000; 352(2): 427-437.

\* cited by examiner

Reber-gBac

Antigen-gp64
(US7,527,967 B2)

Antigen-Bac
(TW I368656)

BACULOVIRUS DISPLAY VECTORS AND USES THEREOF

REFERENCE TO RELATED APPLICATION

The present application claims the priority to U.S. Provisional Application Ser. No. 62/162,139, filed May 15, 2015, which is herein incorporated by reference in its entirety.

FIELD OF THE INVENTION

The present invention relates generally to recombinant baculoviruses.

BACKGROUND OF THE INVENTION

Baculovirus infects insects and is non-pathogenic to humans, but can transduce a broad range of mammalian and avian cells. Thanks to the biosatety, large cloning capacity, low cytotoxicity and non-replication nature in the transduced cells as well as the ease of manipulation and production, baculovirus has gained explosive popularity as a gene delivery vector for a wide variety of applications such as antiviral therapy, cancer therapy, regenerative medicine and vaccine.

U.S. Pat. No. 7,527,967 discloses a recombinant baculovirus that displays a fusion heterologous polypeptide on the surface of the baculovirus for use in generating an antibody or an immune response against a heterologus protein or virus in a subject in need thereof. The fusion heterologous polypeptides therein is made by fusing a heterologus antigen with the carboxyl terminal amino acids from 227 to 529 of baculovirus GP64 protein (FIG. 2C). The construct therein contains a substantial portion of the extracellular domain of GP64 including B12D5 binding site. When it is used in immunization, the extracellular domain of GP64 may elicit an immune response and produce unintended antibodies such as useless anti-GP64 B12D5 antibody (Zhou et al. *Virology* 2006; 352(2):427-437). GP64 B12D5 antibody is a neutralization antibody against baculovirus itself instead of a foreign antigen of interest. In addition, baculovirus is slightly immunogenic to porcine.

Taiwanese Patent No. 1368656 discloses a method of using the signal peptide, transmembrane domain and the cytoplasmic transduction domain from GP64 to present an antigen. The construct therein contains only the transmembrane domain and cytoplasmic trunsduction domain without the extracellular domain of GP64 (FIG. 2D). It has less expression of foreign antigen and is sensitive to inactivation reagents (Premanand et al. *PLoS ONE* 2013; 8(2): e55536).

Therefore, a heretofore unaddressed need exists in the art to address the aforementioned deficiencies and inadequacies, especially in connection with a baculovirus vector that is insensitive to inactivation reagent and has improved immunogenicity.

SUMMARY OF THE INVENTION

In one aspect, the invention relates to a vector comprising a transgene encoding a fusion protein, the fusion protein comprising: (a) a signal peptide located at the N-terminus of the fusion protein; (h) a heterologous antigen; and (c) a C-terminal region of baculovirus envelope GP64 protein, having at least 100 amino acid residues in length and lacking a B12D5 binding epitope located within the central basic region of the GP64 protein; wherein the heterologous antigen is located between the signal peptide and the C-terminal region of the GP64 protein.

In one embodiment of the invention, the vector of the invention is a recombinant baculovirus.

In another aspect, the invention relates to a recombinant baculovirus displaying on its envelop a fusion protein, the fusion protein comprising: (i) a heterologous antigen; and (ii) a C-terminal region of baculovirus envelope GP64 protein, having at least 100 amino acid residues in length and lacking a B12D5 binding epitope located within the central basic region of the GP64 protein.

In one embodiment of the invention, the genome of the recombinant baculovirus comprises a transgene encoding a fusion protein comprising: (a) a signal peptide; (b) the heterologous antigen; and (c) the C-terminal region of the baculovirus envelope GP64 protein wherein the antigen is located between the signal peptide and the C-terminal region of the GP64 protein.

In another embodiment of the invention, the transgene is operably linked to a promoter.

In another embodiment of the invention, the promoter is polyhedrin.

In another embodiment of the invention, the C-terminal region of the GP64 protein has from 186 to 220 amino acids in length.

In another embodiment of the invention, the C-terminal region of the GP64 protein lacks the amino acid sequence of SEQ ID NO: 2, 3, or 4.

In another embodiment of the invention, the C-terminal region of the GP64 protein comprises the amino acids from 293 to 512 of SEQ ID NO: 1.

In another embodiment of the invention, the C-terminal region of the GP64 protein comprises amino acids from 327 to 512 of SEQ ID NO: 1.

In another embodiment of the invention, the C-terminal region of the GP64 protein has an N-terminus between amino acid residues 292 and 328 of SEQ ID NO: 1.

In another embodiment of the invention, the signal peptide comprises an amino acid sequence selected from the group consisting of SEQ ID NOs: 5, 6, 7, 8, 9, 10, 11, and 12.

Further in another aspect, the invention relates to an insect cell or a cell transduced with the vector or the recombinant baculovirus of the invention.

In another embodiment of the invention, the antigen is at least one selected from the group consisting of a pathogen protein, a cancer cell protein, and an immune checkpoint protein.

The pathogen may be at least one selected from the group consisting of human papillomavirus, porcine reproductive and respiratory syndrome virus, human immunodeficiency virus-1. Dengue virus, hepatitis C virus, hepatitis B virus, porcine circovirus 2, classical swine lever virus, foot-and-mouth disease virus. Newcastle disease virus, transmissible gastroenteritis virus, porcine epidemic diarrhea virus, influenza virus, pseudorabies virus, parvovirus, swine vesicular disease virus, poxvirus, rotavirus, *Mycoplasma pneumonia*, herpes virus, infectious bronchitis, infectious bursal disease virus. The cancer may be at least One selected from the group consisting of non-small cell lung cancer, breast carcinoma, melanoma, lymphomas, colon carcinoma, hepatocellular carcinoma, and any combination thereof. The immune cheek point may be at least one selected from the group consisting of PD-1, PD-L1, PD-L2, and CTLA-4.

In another embodiment of the invention, the antigen is at least one selected from the group consisting of classical swine fever virus envelope glycoprotein E2, porcine epidemic diarrhea virus S1 protein, programmed cell death protein 1, and a tumor-associated antigen.

Yet in another aspect, the invention relates to a method for eliciting an antigen-specific immunogenic response in a subject in need thereof, comprising administering to the subject in need thereof a therapeutically effective amount of the vector or the recombinant baculovirus of the invention.

DETAILED DESCRIPTION OF THE INVENTION

Figure 1A:
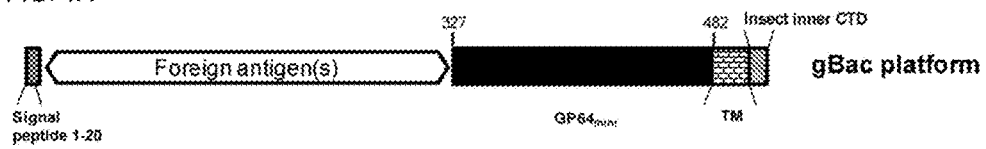
FIG. 1A is a schematic drawing illustrating a baculovirus vector platform design according to one embodiment of the invention.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

A vector is a vehicle used to transfer genetic material to a target cell. A viral vector is a virus modified to deliver foreign genetic material into a cell.

The term "gene transduction", "transduce", or "transduction" is a process by which a foreign DNA is introduced into another cell via a viral vector.

A signal sequence or signal peptide (sometimes referred to as signal sequence, targeting signal, localization signal, localization sequence, transit peptide, leader sequence or leader peptide) is a short (5-30 amino acids long) peptide present at the N-terminus of the majority of newly synthesized proteins that are destined towards the secretory pathway. These proteins include those that reside either inside certain organelles (the endoplasmic reticulum, golgi or endosomes), secreted from the cell, or inserted, into most cellular membranes.

The term "B12D5" refers to a monoclonal antibody against gp64. B12D5 has a binding epitope of KKRPPT-WRHNV (SEQ ID NO: 3) at 277-287 of gp64, or HRVK-KRPPTW (SEQ ID NO: 2) located within the central region from residues 271 to 292 (SEQ ID NO: 4) of gp64. See Zhou et al. (2006) Supra; Wu et al (2012) "A pH-Sensitive Heparin-Binding Sequence from Baculovirus gp64Protein Is Important for Binding to Mammalian Cells but Not to Sf9 Insect Cells" Journal of Virology, Vol. 86 (1) 484-491.

Programmed cell death protein 1, also known as PD-1 and CD279 (cluster of differentiation 279), is a protein that in humans is encoded by the PDCD1 gene. PD-1 is a cell surface receptor that belongs to the immunoglobulin superfamily and is expressed on T cells and pro-B cells. PD-1 binds two ligands. PD-L1 and PD-L2. PD-1, functioning as an immune checkpoint, plays an important role in down regulating the immune system by preventing the activation of T-cells, which in turn reduces autoimmunity and promotes self-tolerance. The inhibitory effect of PD-1 is accomplished through a dual mechanism of promoting apoptosis (programmed cell death) in antigen specific T-cells in lymph nodes while simultaneously reducing apoptosis in regulatory T cells (suppressor T cells). A new class of drugs that block PD-1, the PD-1 inhibitors, activate the immune system to attack tumors and are therefore used with varying success to treat some types of cancer.

An antigen may be a pathogenic protein, polypeptide or peptide that is responsible for a disease caused by the pathogen, or is capable of inducing an immunological response in a host infected by the pathogen, or tumor-associated antigen (TAA) which is a polypeptide specifically expressed in tumor cells. The antigen may be selected from a pathogen or cancer cells including, but not limited to, Human Papillomavirus (HPV), Porcine reproductive and respiratory syndrome virus (PRRSV), Human immunodeficiency virus-1(HIV-1), Dengue virus, Hepatitis C virus (HCV), Hepatitis B virus (HBV), Porcine Circovirus 2 (PCV2), Classical Swine Fever Virus (CSFV), Foot-and-mouth disease virus (FMDV), Newcastle disease virus (NDV), Transmissible gastroenteritis virus (TGEV). Porcine epidemic diarrhea virus (PEDV). Influenza virus, Pseudorabies virus, Parvovirus, Pseudorabies virus, Swine vesicular disease virus (SVDV), Poxvirus, Rotavirus, *Mycoplasma pneumonia*, Herpes virus, infectious bronchitis, or infectious bursal disease virus, non-small cell lung cancer, breast carcinoma, melanoma, lymphomas, colon carcinoma, hepatocellular carcinoma and any combination thereof. For example, HPV E7 protein (E7), HCV core protein (HCV core), HBV X protein (HBx) were selected as antigens for vaccine development. The antigen may be a fusion antigen from a fusion of two or more antigens selected from one or more pathogenic proteins. For example, a fusion antigen of PRRSV ORF6 and ORF5 fragments, or a fusion of antigens from PRRSV and PCV2 pathogens.

Alternatively, an antigen may be an inhibitory immune checkpoint protein such as PD-1, PD-L1, PD-L2, and CTLA-4, etc.

The terms "immune checkpoint protein" and "Immune checkpoint" are interchangeable. Immune checkpoints affect immune system functioning. Immune checkpoints can be stimulatory or inhibitory. Tumors can use these checkpoints to protect themselves from immune system attacks. Checkpoint therapy can block inhibitory checkpoints, restoring immune system function. One ligand-receptor interaction under investigation is the interaction between the transmembrane programmed cell death 1 protein (PDCD1, PD-1; also known as CD279) and its ligand, PD-1 ligand 1 (PD-L1, CD274). PD-L1 on the cell surface binds to PD1 on an immune cell surface, which inhibits immune cell activity. Among PD-L1 functions is a key regulatory role on T cell activities. It appears that (cancer-mediated) upregulation of PD-L1 on the cell surface may inhibit T cells that might otherwise attack. Antibodies that bind to either PD-1 or PD-L1 and therefore block the interaction may allow the T-cells to attack the tumor. Ipilimumab is the first checkpoint antibody approved by the FDA. It blocks inhibitory immune checkpoint CTLA-4.

The term "treating" or "treatment" refers to administration of an effective amount of the fusion protein to a subject in need thereof, who has cancer or infection, or a symptom or predisposition toward such a disease, with the purpose of cure, alleviate, relieve, remedy, ameliorate, or prevent the disease, the symptoms of it, or the predisposition towards it. Such a subject can be identified by a health care professional based on results from any suitable diagnostic method.

The term "an effective amount" refers to the amount of an active compound that is required to confer a therapeutic effect on the treated subject. Effective doses will vary, as recognized by those skilled in the art, depending on rout of administration, excipient usage, and the possibility of co-usage with other therapeutic treatment.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Figure 1B:
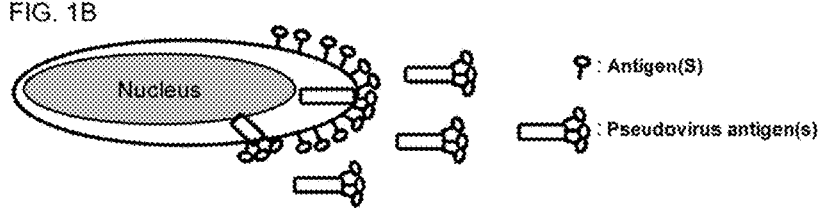
FIG. 1B is a schematic drawing illustrating a foreign antigen or foreign genes not only can be anchored onto the virus envelope but also expressed in the membrane fraction of insect cells by a gBac surface display platform. The rectangle represents a virus.

Construction of Vectors and Generation of Recombinant Baculoviruses, Virus-Like Particles, and Proteins FIG. 1A shows a gBac platform. A foreign gene (e.g., optimized classical swine fever virus (CSFV) E2 or porcine epidemic diarrhea virus (PEDV) spike genes) may be obtained by PCR synthesis and then cloned into a gBac vector through restriction enzyme sites (e.g., SacI/NotI) using IN-FUSION® cloning kit (Clontech). The gBac vector is derived from baculovirus transfer vector pBACPAK™ (GENBANK™ accession No. U02446). Using the gBac surface display platform of FIG. 1A, a foreign antigen or foreign genes can be anchored onto the virus envelope and also expressed in the membrane fraction of insect cells (FIG. 1B).

Figure 2A:
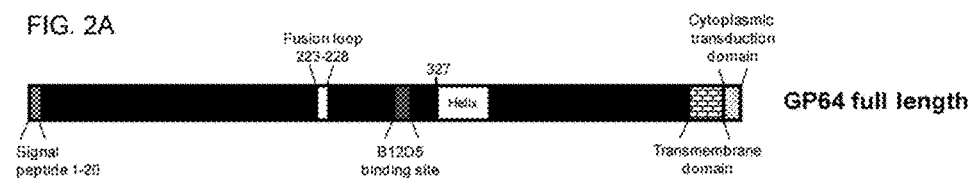
FIG. 2A is a schematic drawing showing a full-length GP64 protein. GP64 minimum ($GP64_{327-482}$), GP64 transmembrane domain (TM) ($GP64_{483-505}$); cytoplasmic transduction domain (CTD) ($GP64_{506-512}$).

FIG. 2A shows a full-length GP64. The baculovirus GP64 envelope fusion protein (GP64 EFP) is the major envelope fusion glycoprotein in some, though not all, baculoviruses. It is found on the surface of both infected cells and budded virions as a homotrimer. Baculovirus enters its host cells by endocytosis followed by a low-pH-induced fusion of the viral envelope with the endosomal membrane, allowing viral entrance into the cell cytoplasm. This membrane fusion, and also the efficient budding of virions from the infected cell, is dependent on GP64.

Figure 2B:
FIG. 2B is a schematic drawing showing a baculovirus vector according to one embodiment of the invention. SP: signal peptide; TM: transmembrane domain, CTD: cytoplasmic transduction domain.
Figure 2C:
FIG. 2C is a schematic drawing showing a baculovirus vector design disclosed in U.S. Pat. No. 7,527,967.
Figure 2D:
FIG. 2D is a schematic drawing showing a baculovirus vector design disclosed in Taiwan Patent No. 1368656.

FIGS. 2B-D show comparisons of three vectors, gBac (or Reber-gBac), antigen-gp64 (or abbreviated as "gp64" disclosed in U.S. Pat. No. 7,527,967), and Antigen-Bac (or abbreviated as "Bac" disclosed in TW 1368656). The gBac vector was constructed using the signal peptide (SP) and a C-terminal region of GP64 from amino acids 327 to 513. The gp64 vector was constructed using the SP and a C-terminal region of GP64 from amino acids 227 to 513. The Bac vector comprises the insect signal peptide (SP), the TM (transmembrane domain) and CTD (cytoplasmic transduction domain) of GP64 and does not comprise the GP64 extracellular domain amino acids. The symbol triangle before the "SP" represents the polyhedrin promoter, which is located-1 site of the insert gene's start codon.

A DNA fragment encoding the SP was generated and amplified by PCR with forward and reverse pirmers 5'-GAGCTCATGGTAAGC-3' (SEQE ID NO: 19) and 5'-AGGCACIAATGCG-3' (SEQ ID NO: 20), respectively. The C-terminal portion of the gp64 gene (encoding GP64 from aa 327 to aa 513) was generated and amplified by PCR using the forward and reverse pirmers 5'-GCGTGTCTGCTCA-3' (SEQ ID NO: 21) and 5'-TIAATATTGTCTA-3' (SEQ ID NO: 22), respectively. The C-terminal portion of the gp64 gene (encoding GP64 from as 227 to as 513 was generated and amplified by PCR using the forward and reverse pirmers 5'-ATCAACAAGCTAA-3' (SEQ ID NO: 23) and 5'-TTAATATTGTCTA-3' (SEQ ID NO: 24), respectively. The above foreign genes were resepctively cloned into the pBACPAK8™ transfer vector.

Using the gBac platform of 2B (or FIG. 1A), we generated two baculovirus vectors: the baculovirus vector CSFV E2-gBac and the baculovirus vector PEDV S1-gBac (FIG. 2B design). The former transduces a gene encoding classical swine fever virus (CSFV) envelope glycoprotein E2, and the latter transduces a gene encoding porcine epidemic diarrhea virus S1 Protein.

For a parallel comparison, we have also used the vectors of FIGS. 2C and 2D and generated two separate baculovirus vectors: the baculovirus vector CSFV E2-gp64 (FIG. 2C design), and the baculovirus vector CSFV E2-Bac (FIG. 2D design) for transducing a foreign gene encoding the antigen CSFV E2.

The fusion genes in the gBac, gp64, and Bac vectors (FIGS. 2B-D designs, respectively) were sequenced to confirm their identities. Recombinant baculovirus viruses containing the recombinant GP64 gene without the transfer vector backbone were generated by homologous recombination. Methods for this construction and recombination are well known in the art. These recombinant viruses were used to prepare antigens. The modified GP64 gene was inserted into a baculovirus transfer vector under the polyhedron promoter by PCR to form the gBac vector. Because the gBac vector has two homologous recombination sites, the original polyhedron locus of wild-type baculovirus is replaced by gBac sequence when co-transfection with gBac plasmid and wild-type baculovirus.

Example 2

Protein Expression and Purification of Antigens

Sf9 cells were used for propagaton and infection of recombiant baculovirus. Baculovirus was propagated in *Spodoptera frugiperda* Sf-9 cell lines and grown at 26° C. in a serum-free medium. The recombinant baculoviruses were produced by infecting Sf-9 cells at an MOI of 5-10 and harvested 3 days after infection. To produce baculovirus on a large scale, the cells may be cultured and infected in bioreactors. The baculovirus fraction were isolated from the culture supernatant of the infected cell. The baculovirus particles were collected by Tangential Flow Filtration (TFF) using a suitable protein cut-off membrane and 0.45 μm sterile membrane.

To test the production of the antigens, the partially purified baculoviruses or infected cell lysates were subjected to 8-10% sodium dodecyl sulfate-polyacrylamide gel electrophoresis (SDS-PAGE) and transferred to nitrocellulose membranes. The foreign antigens were detected by mouse anti-gp64 mAb (available from commercial sources and used at 1:5,000 dilution) as the primary antibody. The secondary antibodies were goat anti-rabbit or goat anti-mouse mAb conjugated with alkaline phosphatase (1:5,000 dilution). The protein hands were visualized by ECL PLUS™ Western Blotting Detection Reagents (GE Healthcare). In the baculovirus surface display system, the forein antigens can be firstly expressed on insect cell membrane, then the budding baculovirus take some of cell membrane to form its envelope. As the result, baculovirus display antigens can be harvested from infected cell lysate (mambrane fraction) and virus surface.

Example 3

Expression of the Antigens by Recombinant Viruses

Before immunization with gBac vaccines, to confirm whether the fusion protein CSFV E2-gBac or PEDV S1-gBac were successfully displayed on the baculovirus envelope, recombinant baculoviruses were collected by centrifugation and TFF. The recombinant baculoviruses were re-suspended in PBS at different concentrations of p.f.u/μl. Incorporation of recombinant proteins into the baculovirus particles were analyzed by Western blotting using anti-gp64 mAb (eBioscience). The fusion protein CSFV E2-gBac was detected at a molecular weight of about 80 kDa and the fusion protein PEDV S1-gBac was detected at a molecular weight of 130 kDa.

Example 4

Vaccine Preparation and Immunization

The recombinant baculoviruses displaying antigens were mixed with water-in-oil-in-water (w/o/w) adjuvant (MONTANIDE ISA 206 VG, SEPPIC.) for vaccine preparation. Female BALB/c mice of 4-week old, purchased from National Experimental Animal Center, Taiwan, R.O.C., were divided into four groups with 5 mice per group. Mice were immunized subcutaneously twice on day 0 and day-14 (FIG. 3) with 200 μl of a solution containing with $10^7$ p.f.u. recombinant baculovirus. The virus of E2-gBac, E2-gp64, and E2-Bac, (FIGS. 2B-D), containing CSFV envelope glycoprotein E2, were inactivated and formulated as vaccines. As negative controls, mice were injected with wild type baculovirus ($10^7$ p.f.u.) or PBS. The blood samples were collected from the caudal vein at week 6. Binary ethylenimine. (BEI) was used to inactivate baculoviruses. It was prepared by dissolving the 0.1 M 2-bromoethylamine hydrobromide (BEA) in 0.2 N NaOH at 37° C. for 1 h. To inactivate the baculovirus, the viral medium was added 4 mM BEI and virus incubated for 16 h at 37° C. After inactivation, sodium thiosulfate ($Na_2S_2O_3$) was added to the medium at a final concentration of 10 times the final BEI concentration to stop the inactivation.

Example 5

Immunogenicity of Antigens Produced by Recombinant Viruses

Figure 3:
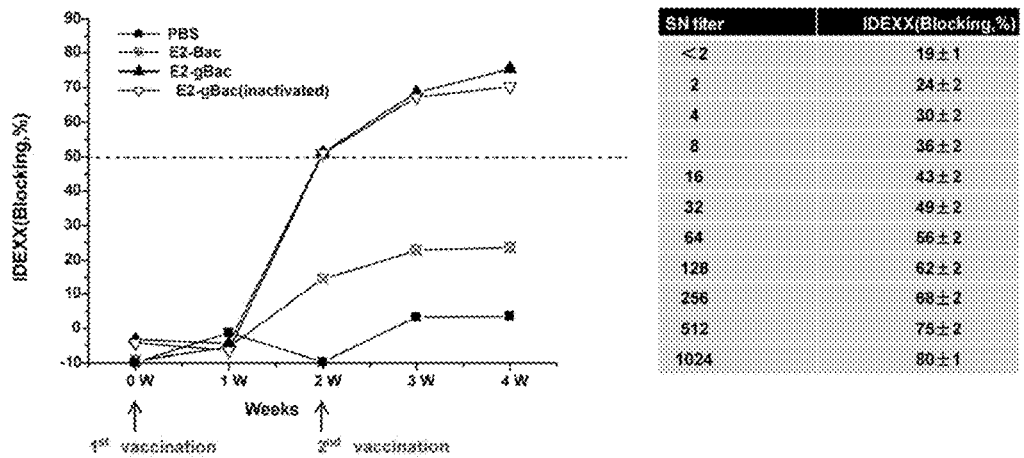
FIG. 3 is a graph showing an immune response induced by baculovirus vectors in mice post vaccination (left panel) and neutralization serum (SN) titer measurement of E2-gBac subunit vaccine (right panel) in mice. Each ELISA value shown is an average value from 5 mice. The difference between the gBac and Bac groups is statistically significant. $P \leq 0.05$. The strain of baculovirus used was AcNPV. The term "SN" stands for neutralization serum. The term "E2-gBac" stands for "baculovirus vector CSFV E2-gBac" according to the vector design of FIG. 2B. The term "E2-gBac (inactivated)" means the baculovirus was inactivated before it was used for immunization. The term "E2-Bac" stands for "baculovirus vector CSFV E2-Bac" according to the vector design of FIG. 2D.

After immunization, the sera of mice were analyzed for the presence of anti-CSFV E2 antibody using the IDEXX CSFV Ab Test Kit (IDEXX) to detect classical swine fever virus (CSFV) antibodies. The degree of CSFV E2-specific antibodies in the serum was calculated as positive when the blocking percentage was above 40% (FIG. 3). The results indicate that the baculovirus vector displayed the fusion protein CSFV E2-Bac. FIG. 3 show that the baculovirus vector CSFV E2-gBac, whether the baculovirus was inactivated or not, induced a much higher anti-CSFV E2 antibody titer than the baculovirus vector CSFV E2-Bac in mice.

We have also compared the effects of the three baculovirus vectors in inducing immunogenic responses in pigs. Three SPF (specific pathogen free) pigs were immunized twice (6-week-old and 9-week-old) via intramuscular route with $10^8$ pfu of recombinant baculovirus vectors E2-gBac, E2-gp64, E2-Bac, and PBS, respectively. After immunization, the sera of piglets were analyzed for the presence of CSFV E2 antibody using IDEXX CSFV Ab Test Kit (IDEXX). The degree of CSFV E2 specific neutralization antibody in the serum was calculated as positive and efficient when the blocking percentage was above 43%.

Figure 4:
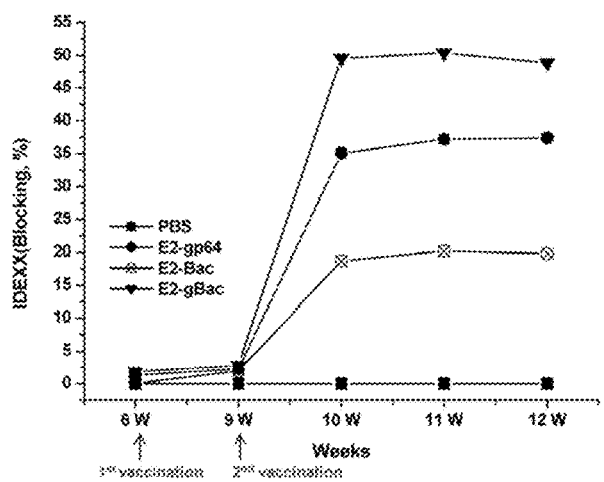
FIG. 4 is a graph showing an immune response induced by baculovirus vectors in pigs post vaccination. Each ELISA value shown is an average value from 3 pigs. The difference between the gBac and gp64 groups is statistically significant. $P \leq 0.05$. The term "E2-gp64" stands for "baculovirus vector CSFV E2-gp64" according to the vector design of FIG. 2C.

As shown in FIG. 4, pigs immunized with E2-gBac were able to survive the CSFV challenge. It indicates that competent neutralization antibody had been induced in the pigs (SN titer≥16, IDEXX blocking ratio≥43%). This proves that the gBac platform is a vaccine platform. FIG. 4 shows that the baculovirus vector CSFV E2-gBac induced a much higher anti-CSFV E2 antibody titer than the baculovirus vectors CSFV E2-Bac and CSFV E2-gp64 in pigs. The results indicate that the gBac surface display platform of the invention can induce a stronger immunity than the priro art baculovirus vectors.

Figure 5:
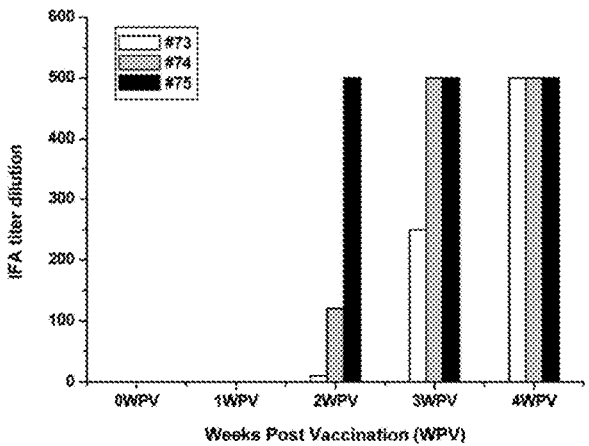
FIG. 5 is a graph showing antibody titers against porcine epidemic diarrhea virus (PEDV) in 3 specific pathogen-free (SPF) pigs post vaccination with the baculovirus vector PEDV S1-gBac. The 3 SPF pigs were labeled as number 73, 74 and 75, respectively. The tem "IFA" stands for immunofluorescent antibody. The results indicated that the serum from the vaccinated pigs could be recognized by PED virus.

We have also gerenated baculovirus vector for transducing porcine epidemic diarrhea virus S1 protein (PEDV S1) into cells for vaccination applications. We tested its effects in inducing an immunogenic response. Briefly, three 9-week-old SPF pigs (labeled as number 73, 74 and 75, respectively) were each immunized twice via an intramuscular route with $10^8$ pfu of recombinant baculovirus vector PEDV S1-gBac or PBS. After immunization, the sera of pigs (from 1 to 4 weeks post vaccination) were analyzed for the presence of anti-PEDV antibodies using an ELISA assay of PED virus. FIG. 5 shows that the baculovirus vector PEDV S1-gBac induced antibody titers against porcine epidemic diarrhea virus in all 3 pigs.

Figure 6A:
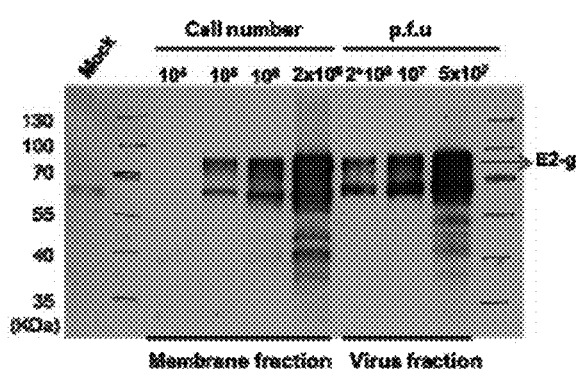
FIGS. 6A-B are photographs of western blot showing that the antigens E2 of CSFV E2-gBac (FIG. 6A) and S1 of PEDV S1-gBac (FIG. 6B) from the Sf9 cell samples were detected.
Figure 6B:
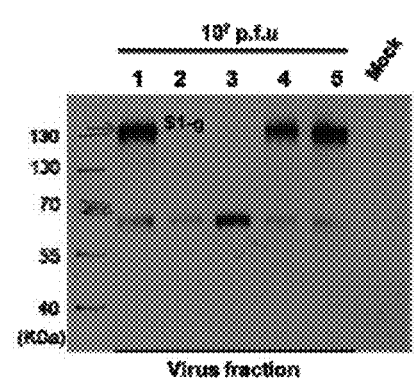
Figure 6C:
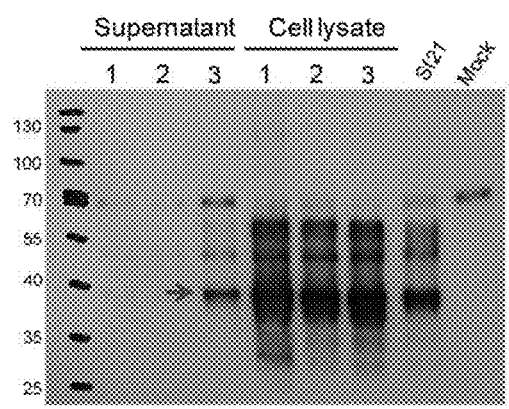
FIGS. 6C-D are photographs of western blot showing that the antigens of hPD-1-gBac in the samples were recognized and detected by anti-gp64 mAb (left panel) and human PD-1 antibody (right panel), respectively.
Figure 6D:
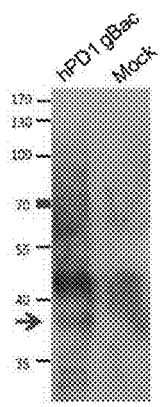

FIGS. 6A-B are photographs of Western blots showing that the antigens E2 of CSFV E2-gBac (FIG. 6A) and S1 of PEDV S1-gBac (FIG. 6B) from the Sf9 cell samples were detected. The cell lysates and collected virus were loaded by different cell number and virus titer. We have also constructed the baculovirus vector human programmed cell death protein 1 (hPD-1gBac)-gBac (hPD-1gBac). To test the production of the antigen, the recombinant baculoviruses or infected cell lysates were subjected to 8-10% sodium dodecyl sulfate-polyacrylamide gel electrophoresis (SDS-PAGE) and transferred to nitrocellulose membranes. The foreign antigens were detected by a mouse anti-gp64 mAb (FIG. 6C) and anti-PDCD-1 antibody (FIG. 6D) (Santa Cruz Biotechnology, Santa Cruz, Calif.) as the primary antibodies. The protein bands were visualized by ECL PLUS™ Western Blotting Detection Reagents (GE Healthcare). FIG. 6D shows that the baculovirus displayed human PD-1 antigen on the envelope, and the displayed PD-1 antigen could be recognized by commercial anti-PDCD-1 antibody (Santa Cruz Biotechnology, Santa Cruz, Calif.).

In summary, the vector of the invention is insensitive to inactivation reagents (FIG. 3) and exhibits higher immunogenicity (FIG. 4). Table 1 shows peptide sequences and SEQ ID NOs.

TABLE 1

| Protein or peptide | Amino acid sequence* (SEQ ID NO:) | a.a. length |
|---|---|---|
| Full length GP64 | *MVSAIVLYVLLAAAAHSAFA*AEHCNAQMKTGPYKIKNLDITPPKETLQKD VEITIVETDYNENVIIGYKGYYQAYAYNGGSLDPNTRVEETMKTLNVGKE DLLMWSIRQQCEVGEELIDRWGSDSDDCFRDNEGRGQWVKGKELVKRQNN NHFAHHTCNKSWRCGISTSKMYSRLECQDDTDECQVYILDAEGNPINVTV DTVLHRDGVSMILKQKSTFTTRQIKAACLLIKDDKNNPESVTREHCLIDN DIYDLSKNTWNCKFNRCIKRKVEHRVKKRPPTWRHNVRAKYTEGDTATKG DLMHIQEELMYENDLLKMNIELMHAHINKLNNMLHDLIVSVAKVDERLIG NLMNNSVSSTFLSDDTFLLMPCTNPPAHTSNCYNNSIYKEGRWVANTDSS QCIDFSNYKELAIDDDVEFWIPTIGNTTYHDSWKDASGWSFIAQQKSNLI TTMENTKFGGVGTSLSDITSMAEGELAAKLTSFMFGHVVNFIILIVILFL YCMIRNRNRQY (SEQ ID NO: 1) | 512 |
| B12D5 binding epitope | HRVKKRPPTW (SEQ ID NO: 2, 292-301 of GP64). | |
| B12D5 binding epitope | KKRPPTWRHNV (277-287 of gp64; SEQ ID NO: 3) | |
| Gp64 central basic region | KVEHRVKKRPPTWRHNVRAKYT (271-292 of gp64; SEQ ID NO: 4) | |
| GP64 signal peptide (SP) | MVSAIVLYVLLAAAAHSAFA ($GP64_{1-20}$; SEQ ID NO: 5) | 20 |

TABLE 1-continued

| Protein or peptide | Amino acid sequence* (SEQ ID NO:) | a.a. length |
|---|---|---|
| 30K protein Bombyx mori | MRLTLFAFVLAVCALASNA (SEQ ID NO: 6) | |
| SP1 *Bombyx mori* | MRVLVLLACLAAASA (SEQ ID NO: 7) | |
| SP2 *Bombyx mori* | MKSVLILAGLVAVALSSAVPKP (SEQ ID NO: 8) | |
| Bombyxin A-4 | MKILLAIALMLSTVMWVST (SEQ ID NO: 9) | |
| Vitellogenin | MKLFVLAAIIAAVSS (SEQ ID NO: 10) | |
| Chitinase precursor | MRAIFATLAVLASCAALVQS (SEQ ID NO: 11) | |
| Adipokintic hormone | MYKLTVFLMFIAF VIIAGAQSMASLTRQDLA (SEQ ID NO: 12) | |
| CSFV E2 (Classical swine fever virus (CSFV) envelope glycoprotein E2) CSFV 96 TD | MLRGQVVQGIIWLLLVTGAQGRLSCKEDHRYAISSTNEIGPLGAEGLTTT WKEYNHGLQLDDGTVRAICIAGSFKVTALNVVSRRYLASLHKRALPTSVT FELLFDGTSPAIEEMGDDFGFGLCPFDTTPVVKGKYNTTLLNGSAFYLVC PIGWTGVIECTAVSPTTLRTEVVKTFKREKPFPHRVDCVTTIVEKEDLFY CKLGGNWTCVKGNPVTYTGGQVRQCRWCGFDFKEPDGLPHYPIGCILTNE TGYRVVDSPDCNRDGVVISTEGEHECLIGNTTVKVHALDGRLAPMPCRPK EIVSSAGPVRKTSCTFNYTKTLRNKYYEPRDSYFQQYMLKGEYQYWFDLD VTDHHTDYFAEF (SEQ ID NO: 13) | 363 |
| PEDV S1 (Procine Epidemic Diarrhea Virus S1 Protein) PEDV USA/Iowa/1898 April 2013 | CSANTNFRRFFSKFNVQAPAVVLGGYLPIGENQGVNSTWYCAGQHPTAS GVHGIFVSHIRGGHGFEIGISQEPFDPSGYQLYLHKATNGNTNATARLRI CQFPSIKTLGPTANNDVTTGRNCLFNKAIPAHMSEHSVVGITWDNDRVTV FSDKIYYFYFKNDWSRVATKCYNSGGCAMQYVYEPTYYMLNVTSAGEDGI SYQPCTANCIGYAANVFATEPNGHIPEGFSFNNWFLLSNDSTLVHGKVVS NQPLLVNCLLAIPKIYGLGQFFSFNQTIDGVCNGAAVQRAPEALRFNIND TSVILAEGSIVLHTALGTNFSFVCSNSSNPHLATFAIPLGATQVPYYCFF KVDTYNSTVYKFLAVLPPTVREIVITKYGDVYVNGFGYLHLGLLDAVTIN FTGHGTDDDVSGFWTIASTNFVDALIEVQGTAIQRILYCDDPVSQLKCSQ VAFDLDDGFYPISSRNLLSHEQPISFVTLPSFNDHSFVNITVSASFGGHS GANLIASDTTINGFSSFCVDTRQFTISLFYNVTNSYGYVSKSQDSNCPFT LQSVNDYLSFSKFCVSTSLLASACTIDLFGYPEFGSGVKFTSLYFQFTKG ELITGTPKPLEGVTDVSFMTLDVCTKYTIYGFKGEGIITLTNSSFLAGVY YTSDSGQLLAFKNVTSGAVYSVTPCSFSEQAAYVDDDIVGVISSLSSSTF NSTRELPG (SEQ ID NO: 14) | 708 |
| Human PD-1 (Programmed cell death protein 1) | QIPQAPWPVVVAWLQLGWRPGWFLDSPDRPWNPPTFFPALLVVTEGDNAT FTCSFSNTSESFVLNWYRMSPSNQTDKLAAFPEDRSQPGQDCRFRVTQLP NGRDFHMSVVRARRNDSGTYLCGAISLAPKAQIKESLAELRVTERRAEVP TAHPSPSPRPAGQFQTDIY (SEQ ID NO: 15) | 170 |
| E2-gBac protein (SP-E2-GP64 mini-TM/CTD) | *MVSAIVLYVLLAAAAHSAFA*MLRGQVVQGIIWLLLVTGAQGRLSCKEDHR YAISSTNEIGPLGAEGLTTTWKEYNHGLQLDDGTVRAICIAGSFKVTALN VVSRRYLASLHKRALPTSVTFELLFDGTSPAIEEMGDDFGFGLCPFDTTP VVKGKYNTTLLNGSAFYLVCPIGWTGVIECTAVSPTTLRTEVVKTFKREK PFPHRVDCVTTIVEKEDLFYCKLGGNWTCVKGNPVTTGGQVRQCRWCGFD FDEPDGLPHYPIGKCILTNETGYRVVDSPDCNRDGVVISTEGEHECLIGN TTVKVHALDGRLAPMPCRPKEIVSSAGPVRKTSCTFNYTKTLRNKYYEPR DSYFQQYMLKGEYQYWFDLDVTDHHTDYFAEF<u>INKLNNMLHDLIVSVAKV DERLIGNLMNNSVSSTFLSDDTFLLMPCTNPPAHTSNYCYNNSIYKEGRW VANTDSSQCIDFSNYKELAIDDDVEFWIPTIGNTTYHDSWKDASGWSFIA QQKSNLITTMENTKFGGVGTSLSDITSMAEGELAAKLTS</u>FMGHVVNFVII IVILFLYCMIRNRNRQY (SEQ ID NO: 16) | 569 |
| S1-gBac protein (SP-S1-GP64 mini-TM/CTD) | *MVSAIVLYVLLAAAAHSAFA*CSANTNFRRFFSKFNVQAPAVVLGGYLPI GENQGVNSTWYCAGQHPTASGVHGIFVSHIRGGHGFEIGISQEPFDPSGY QLYLHKATNGNTNATARLRICQFPSIKTLGPTANNDVTTGRNCLFNKAIP AHMSEHSVVGITWDNDRVTVFSDKIYYFYFKNDWSRVATKCYNSGGCAMQ YVYEPTYYMLNVTSAGEDGISYQPCTANCIGYAANVFATEPNGHIPEGFS FNNWFLLSNDSTLVHGKVVSNQPLLVNCLLAIPKIYGLGQFFSFNQTIDG VCNGAAVQRAPEALRFNINDTSVILAEGSIVLHTALGTNFSFVCSNSSNP HLATFAIPLGATQVPYYCFFKVDTYNSTVYKFLAVLPPTVREIVITKYGD VYVNGFGYLHLGLLDAVTINFTGHGTDDDVSGFWTIASTNFVDALIEVQG | 914 |

TABLE 1-continued

| Protein or peptide | Amino acid sequence* (SEQ ID NO:) | a.a. length |
|---|---|---|
| | TAIQRILYCDDPVSQLKCSQVAFDLDDGFYPISSRNLLSHEQPISFVTLP<br>SFNDHSFVNITVSASFGGHSGANLIASDTTINGFSSFCVDTRQFTISLFY<br>NVTNSYGYVSKSQDSNCPFTLQSVNDYLSFSKFCVSTSLLASACTIDLFG<br>YPEFGSGVKFTSLYFQFTKGELITGTPKPLEGVTDVSFMTLDVCTKYTIY<br>GFKGEGHTLTNSSFLAGYVYYTSDSGQLLAFKNVTSGAVYSVTPCSFSEQ<br>AAYVDDDIVGVISSLSSSTFNSTRELPG<u>INKLNNMLHDLIVSVAKVDERL<br>IGNLMNNSVSSTFLSDDTFLLMPCTNPPAHTSNCYNNSIYKEGRWVANTD<br>SSQCIDFSNYEKLAIDDDVEFWIPTIGNTTYHDSWKDASGWSFIAQQKSN<br>LITTMENTKFGGVGTSLSDITSMAEGELAAKLTS</u>FMFGHVVNFVIILIVI<br>LFLYCMI*RNRNRQY*<br>(SEQ ID NO: 17) | |
| hPD1-gBac<br>protein<br>(SP-hPD1-GP64<br>mini-TM/CTD) | *<u>MVSAIVLYVLLAAAAHSAFA</u>*QIPQAPWPVVWAVLQLGWRPGWFLDSPDRP<br>WNPPTFFPALLVVTEGDNATFTCSFSNTSESFVLNWYRMSPSNQTDKLAA<br>FPEDRSQPGQDCRFRVTQLPNGRDFHMSVVRARRNDSGTYLCGAISLAPK<br>AQIKESLRAELRVTERRAEVPTAHPSPSPRPAGQFQTDIY<u>INKLNNMLHD<br>LIVSVAKVDERLIGNLMNNSVSSTFLSDDTFLLMPCTNPPAHTSNCYNNS<br>IYKEGRWVANTDSSQCIDFSNYKELAIDDDVEFWIPTIGNTTYHDSWKDA<br>SGWSFIAQQKSNLITTMENTKFGGVGTLSLSDITSMAEGELAAKLTS</u>FMF<br>GHVVNFNIILIVILFLYCMI*RNRNRQY*<br>(SEQ ID NO: 18) | 376 |

*Full length GP64: The GP64 Signal peptide (SP) (GP64$_{1-20}$) is underlined and in italics. The GP64 minimum (GP64$_{327-482}$) is underlined without italics. The GP64 transmembrane domain (TM) (GP64$_{483-505}$) is in bold only. The GP64 cytoplasmic transduction domain (CTD) (GP64$_{506-512}$) is in italics only.
E2-gBac protein (SP-E2-GP64 mini-TM/CTD): The GP64 Signal peptide (SP) (GP64$_{1-20}$) is underlined and in italics. The GP64 minimum (GP64$_{327-482}$) is underlined without italics. The GP64 transmembrane domain (TM) (GP64$_{483-505}$) is in bold only. The GP64 cytoplasmic transduction domain (CTD) (GP64$_{506-512}$) is in italics only.
S1-gBac protein (SP-S1-GP64 mini-TM/CTD): The GP64 Signal peptide (SP) (GP64$_{1-20}$) is underlined and in italics. The GP64 minimum (GP64$_{327-482}$) is underlined without italics. The GP64 transmembrane domain (TM) (GP64$_{483-505}$) is in bold only. The GP64 cytoplasmic transduction domain (CTD) (GP64$_{506-512}$) is in italics only.
hPD1-gBac protein (SP-hPD1-GP64 mini-TM/CTD): The GP64 Signal peptide (SP) (GP64$_{1-20}$) is underlined and in italics. The GP64 minimum (GP64$_{327-482}$) is underlined without italics. The GP64 transmembrane domain (TM) (GP64$_{483-505}$) is in bold only. The GP64 cytoplasmic transduction domain (CTD) (GP64$_{506-512}$) is in italics only.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the appended claims.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion or such references is provided merely to clarify the description of the present invention and is not an admission, that any such reference is "prior art" to the invention described herein. All references cited and discussed in this specification are incorporated herein by reference in their entireties and to the same extent as if each reference was individually incorporated by reference.

What is claimed is:

1. A vector comprising a transgene encoding a fusion protein, the fusion protein comprising:
   (a) a signal peptide located at the N-terminus of the fusion protein:
   (b) a heterologous antigen; and
   (c) a C-terminal region of baculovirus envelope GP64 protein, having at least 100 amino acid residues in length and lacking a B12D5 binding epitope located within the central basic region of the GP64 protein, the B12D5 binding epitope comprising the amino acid sequence of SEQ ID NO: 2 or 3;
   wherein the heterologous antigen is located between the signal peptide and the C-terminal region of the GP64 protein.

2. The vector of claim 1, which is a recombinant baculovirus.

3. A recombinant baculovirus displaying on its envelope a fusion protein, the fusion protein comprising:
   (i) a heterologous antigen; and
   (ii) a C-terminal region of baculovirus envelope GP64 protein, having at least 100 amino acid residues in length and lacking a B12D5 binding epitope located within the central basic region of the GP64 protein, the B12D5 binding epitope comprising the amino acid sequence of SEQ ID NO: 2 or 3.

4. The recombinant baculovirus of claim 3, the genome of which comprises a transgene encoding a fusion protein comprising:
   (a) a signal peptide;
   (b) the heterologous antigen; and
   (c) the C-terminal region of the baculovirus envelope GP64 protein;
   wherein the antigen is located between the signal peptide and the C-terminal region of the GP64protein.

5. The recombinant baculovirus of claim 3, wherein the transgene is operably linked to a promoter.

6. The recombinant baculovirus of claim 3, wherein the N-terminus of the C-terminal region of the GP64 protein is located between amino acid residue 292 and amino acid residue 328 of SEQ ID NO: 1.

7. The recombinant baculovirus of claim 4, wherein the signal peptide comprises an amino acid sequence selected from the group consisting of SEQ ID NOs: 5, 6, 7, 8, 9, 10, 11, and 12.

8. An insect cell transduced with the recombinant baculovirus of claim 3.

9. The recombinant baculovirus of claim 3, wherein the antigen is at least one selected from the group consisting of a pathogen protein, a cancer cell protein, and an immune checkpoint protein.

10. The recombinant baculovirus of claim 9, wherein:
    (i) the pathogen is at least one selected from the group consisting of human papillomavirus, porcine reproductive and respiratory syndrome virus, human immunodeficiency virus-1, Dengue virus, hepatitis C virus, hepatitis B virus, porcine circovirus 2, classical swine fever virus, foot-and-mouth disease virus, Newcastle disease virus, transmissible gastroenteritis virus, porcine epidemic diarrhea virus, influenza virus, pseudorabies virus, parvovirus, swine vesicular disease virus, poxvirus, rotavirus, Mycoplasma pneumonia, herpes virus, infectious bronchitis, and infectious bursal disease virus;
    (ii) the cancer is at least one selected from the group consisting of non-small cell lung cancer, breast carcinoma, melanoma, lymphomas, colon carcinoma, hepatocellular carcinoma, and any combination thereof; and
    (iii) the immune check point is at least one selected from the group consisting of PD-1, PD-L1, PD-L2, and CTLA-4.

11. The recombinant baculovirus of claim 3, wherein the antigen is at least one selected from the group consisting of classical swine fever virus envelope glycoprotein E2, porcine epidemic diarrhea virus S1 protein, programmed cell death protein 1, and a tumor-associated antigen.

12. The vector of claim 1, wherein the antigen is at least one selected from the group consisting of a pathogen protein, a cancer cell protein, and an immune checkpoint protein.

13. The vector of claim 1, wherein the C-terminal region of the GP64 protein-comprises the amino acids from 327 to 512 of SEQ ID NO: 1.

14. A method for eliciting an antigen-specific immunogenic response in a subject in need thereof, comprising:
    administering to the subject in need thereof a therapeutically effective amount of the recombinant baculovirus of claim 3.

15. The recombinant baculovirus of claim 6, wherein the antigen is at least one selected from the group consisting, of a pathogen protein, a cancer cell protein, and an immune checkpoint protein.

16. The recombinant baculovirus of claim 6, wherein the C-terminal region of the GP64 protein comprises the amino acids from 293 to 512 or comprises the amino acids from 327 to 512 of SEQ ID NO: 1.

17. The recombinant baculovirus of claim 3, wherein the C-terminal region of the GP64 protein comprises the amino acids from 293 to 512 or comprises the amino acids from 327to 512 of SEQ ID NO: 1.

* * * * *

SEQUENCE LISTING

```
<160> NUMBER OF SEQ ID NOS: 24

<210> SEQ ID NO 1
<211> LENGTH: 512
<212> TYPE: PRT
<213> ORGANISM: Autographa californica nucleopolyhedrovirus

<400> SEQUENCE: 1

Met Val Ser Ala Ile Val Leu Tyr Val Leu Leu Ala Ala Ala Ala His
1               5                   10                  15

Ser Ala Phe Ala Ala Glu His Cys Asn Ala Gln Met Lys Thr Gly Pro
```

```
                    20                  25                  30
        Tyr Lys Ile Lys Asn Leu Asp Ile Thr Pro Lys Glu Thr Leu Gln
                        35                  40                  45
        Lys Asp Val Glu Ile Thr Ile Val Glu Thr Asp Tyr Asn Glu Asn Val
         50                  55                  60
        Ile Ile Gly Tyr Lys Gly Tyr Tyr Gln Ala Tyr Ala Tyr Asn Gly Gly
         65                  70                  75                  80
        Ser Leu Asp Pro Asn Thr Arg Val Glu Thr Met Lys Thr Leu Asn
                        85                  90                  95
        Val Gly Lys Glu Asp Leu Leu Met Trp Ser Ile Arg Gln Gln Cys Glu
                       100                 105                 110
        Val Gly Glu Glu Leu Ile Asp Arg Trp Gly Ser Asp Ser Asp Cys
                       115                 120                 125
        Phe Arg Asp Asn Glu Gly Arg Gly Gln Trp Val Lys Gly Lys Glu Leu
                       130                 135                 140
        Val Lys Arg Gln Asn Asn Asn His Phe Ala His His Thr Cys Asn Lys
        145                 150                 155                 160
        Ser Trp Arg Cys Gly Ile Ser Thr Ser Lys Met Tyr Ser Arg Leu Glu
                       165                 170                 175
        Cys Gln Asp Asp Thr Asp Glu Cys Gln Val Tyr Ile Leu Asp Ala Glu
                       180                 185                 190
        Gly Asn Pro Ile Asn Val Thr Val Asp Thr Val Leu His Arg Asp Gly
                       195                 200                 205
        Val Ser Met Ile Leu Lys Gln Lys Ser Thr Phe Thr Thr Arg Gln Ile
                       210                 215                 220
        Lys Ala Ala Cys Leu Leu Ile Lys Asp Asp Lys Asn Asn Pro Glu Ser
        225                 230                 235                 240
        Val Thr Arg Glu His Cys Leu Ile Asp Asn Asp Ile Tyr Asp Leu Ser
                       245                 250                 255
        Lys Asn Thr Trp Asn Cys Lys Phe Asn Arg Cys Ile Lys Arg Lys Val
                       260                 265                 270
        Glu His Arg Val Lys Lys Arg Pro Pro Thr Trp Arg His Asn Val Arg
                       275                 280                 285
        Ala Lys Tyr Thr Glu Gly Asp Thr Ala Thr Lys Gly Asp Leu Met His
                       290                 295                 300
        Ile Gln Glu Glu Leu Met Tyr Glu Asn Asp Leu Leu Lys Met Asn Ile
        305                 310                 315                 320
        Glu Leu Met His Ala His Ile Asn Lys Leu Asn Asn Met Leu His Asp
                       325                 330                 335
        Leu Ile Val Ser Val Ala Lys Val Asp Glu Arg Leu Ile Gly Asn Leu
                       340                 345                 350
        Met Asn Asn Ser Val Ser Ser Thr Phe Leu Ser Asp Asp Thr Phe Leu
                       355                 360                 365
        Leu Met Pro Cys Thr Asn Pro Pro Ala His Thr Ser Asn Cys Tyr Asn
                       370                 375                 380
        Asn Ser Ile Tyr Lys Glu Gly Arg Trp Val Ala Asn Thr Asp Ser Ser
        385                 390                 395                 400
        Gln Cys Ile Asp Phe Ser Asn Tyr Lys Glu Leu Ala Ile Asp Asp
                       405                 410                 415
        Val Glu Phe Trp Ile Pro Thr Ile Gly Asn Thr Thr Tyr His Asp Ser
                       420                 425                 430
        Trp Lys Asp Ala Ser Gly Trp Ser Phe Ile Ala Gln Gln Lys Ser Asn
                       435                 440                 445
```

```
Leu Ile Thr Thr Met Glu Asn Thr Lys Phe Gly Gly Val Gly Thr Ser
    450                 455                 460
Leu Ser Asp Ile Thr Ser Met Ala Glu Gly Glu Leu Ala Ala Lys Leu
465                 470                 475                 480
Thr Ser Phe Met Phe Gly His Val Val Asn Phe Val Ile Ile Leu Ile
                485                 490                 495
Val Ile Leu Phe Leu Tyr Cys Met Ile Arg Asn Arg Asn Arg Gln Tyr
                500                 505                 510
```

<210> SEQ ID NO 2
<211> LENGTH: 10
<212> TYPE: PRT
<213> ORGANISM: Autographa californica nucleopolyhedrovirus

<400> SEQUENCE: 2

```
His Arg Val Lys Lys Arg Pro Pro Thr Trp
1               5                   10
```

<210> SEQ ID NO 3
<211> LENGTH: 11
<212> TYPE: PRT
<213> ORGANISM: Autographa californica nucleopolyhedrovirus

<400> SEQUENCE: 3

```
Lys Lys Arg Pro Pro Thr Trp Arg His Asn Val
1               5                   10
```

<210> SEQ ID NO 4
<211> LENGTH: 22
<212> TYPE: PRT
<213> ORGANISM: Autographa californica nucleopolyhedrovirus

<400> SEQUENCE: 4

```
Lys Val Glu His Arg Val Lys Lys Arg Pro Pro Thr Trp Arg His Asn
1               5                   10                  15

Val Arg Ala Lys Tyr Thr
            20
```

<210> SEQ ID NO 5
<211> LENGTH: 20
<212> TYPE: PRT
<213> ORGANISM: Autographa californica nucleopolyhedrovirus

<400> SEQUENCE: 5

```
Met Val Ser Ala Ile Val Leu Tyr Val Leu Leu Ala Ala Ala Ala His
1               5                   10                  15

Ser Ala Phe Ala
            20
```

<210> SEQ ID NO 6
<211> LENGTH: 19
<212> TYPE: PRT
<213> ORGANISM: Bombyx mori

<400> SEQUENCE: 6

```
Met Arg Leu Thr Leu Phe Ala Phe Val Leu Ala Val Cys Ala Leu Ala
1               5                   10                  15

Ser Asn Ala
```

<210> SEQ ID NO 7
<211> LENGTH: 15

<212> TYPE: PRT
<213> ORGANISM: Bombyx mori

<400> SEQUENCE: 7

Met Arg Val Leu Val Leu Leu Ala Cys Leu Ala Ala Ala Ser Ala
1               5                   10                  15

<210> SEQ ID NO 8
<211> LENGTH: 22
<212> TYPE: PRT
<213> ORGANISM: Bombyx mori

<400> SEQUENCE: 8

Met Lys Ser Val Leu Ile Leu Ala Gly Leu Val Ala Val Ala Leu Ser
1               5                   10                  15

Ser Ala Val Pro Lys Pro
            20

<210> SEQ ID NO 9
<211> LENGTH: 19
<212> TYPE: PRT
<213> ORGANISM: Bombyx mori

<400> SEQUENCE: 9

Met Lys Ile Leu Leu Ala Ile Ala Leu Met Leu Ser Thr Val Met Trp
1               5                   10                  15

Val Ser Thr

<210> SEQ ID NO 10
<211> LENGTH: 15
<212> TYPE: PRT
<213> ORGANISM: Bombyx mandarina

<400> SEQUENCE: 10

Met Lys Leu Phe Val Leu Ala Ala Ile Ile Ala Ala Val Ser Ser
1               5                   10                  15

<210> SEQ ID NO 11
<211> LENGTH: 20
<212> TYPE: PRT
<213> ORGANISM: Bombyx mori

<400> SEQUENCE: 11

Met Arg Ala Ile Phe Ala Thr Leu Ala Val Leu Ala Ser Cys Ala Ala
1               5                   10                  15

Leu Val Gln Ser
            20

<210> SEQ ID NO 12
<211> LENGTH: 31
<212> TYPE: PRT
<213> ORGANISM: Bombyx mori

<400> SEQUENCE: 12

Met Tyr Lys Leu Thr Val Phe Leu Met Phe Ile Ala Phe Val Ile Ile
1               5                   10                  15

Ala Gly Ala Gln Ser Met Ala Ser Leu Thr Arg Gln Asp Leu Ala
            20                  25                  30

<210> SEQ ID NO 13
<211> LENGTH: 363
<212> TYPE: PRT
<213> ORGANISM: Classical swine fever virus

<400> SEQUENCE: 13

```
Met Leu Arg Gly Gln Val Val Gln Gly Ile Ile Trp Leu Leu Leu Val
1               5                   10                  15

Thr Gly Ala Gln Gly Arg Leu Ser Cys Lys Glu Asp His Arg Tyr Ala
            20                  25                  30

Ile Ser Ser Thr Asn Glu Ile Gly Pro Leu Gly Ala Glu Gly Leu Thr
        35                  40                  45

Thr Thr Trp Lys Glu Tyr Asn His Gly Leu Gln Leu Asp Asp Gly Thr
    50                  55                  60

Val Arg Ala Ile Cys Ile Ala Gly Ser Phe Lys Val Thr Ala Leu Asn
65                  70                  75                  80

Val Val Ser Arg Arg Tyr Leu Ala Ser Leu His Lys Arg Ala Leu Pro
                85                  90                  95

Thr Ser Val Thr Phe Glu Leu Leu Phe Asp Gly Thr Ser Pro Ala Ile
            100                 105                 110

Glu Glu Met Gly Asp Asp Phe Gly Phe Gly Leu Cys Pro Phe Asp Thr
        115                 120                 125

Thr Pro Val Val Lys Gly Lys Tyr Asn Thr Thr Leu Leu Asn Gly Ser
    130                 135                 140

Ala Phe Tyr Leu Val Cys Pro Ile Gly Trp Thr Gly Val Ile Glu Cys
145                 150                 155                 160

Thr Ala Val Ser Pro Thr Thr Leu Arg Thr Glu Val Val Lys Thr Phe
                165                 170                 175

Lys Arg Glu Lys Pro Phe Pro His Arg Val Asp Cys Val Thr Thr Ile
            180                 185                 190

Val Glu Lys Glu Asp Leu Phe Tyr Cys Lys Leu Gly Gly Asn Trp Thr
        195                 200                 205

Cys Val Lys Gly Asn Pro Val Thr Tyr Thr Gly Gly Gln Val Arg Gln
    210                 215                 220

Cys Arg Trp Cys Gly Phe Asp Phe Lys Glu Pro Asp Gly Leu Pro His
225                 230                 235                 240

Tyr Pro Ile Gly Lys Cys Ile Leu Thr Asn Glu Thr Gly Tyr Arg Val
                245                 250                 255

Val Asp Ser Pro Asp Cys Asn Arg Asp Gly Val Val Ile Ser Thr Glu
            260                 265                 270

Gly Glu His Glu Cys Leu Ile Gly Asn Thr Thr Val Lys Val His Ala
        275                 280                 285

Leu Asp Gly Arg Leu Ala Pro Met Pro Cys Arg Pro Lys Glu Ile Val
    290                 295                 300

Ser Ser Ala Gly Pro Val Arg Lys Thr Ser Cys Thr Phe Asn Tyr Thr
305                 310                 315                 320

Lys Thr Leu Arg Asn Lys Tyr Tyr Glu Pro Arg Asp Ser Tyr Phe Gln
                325                 330                 335

Gln Tyr Met Leu Lys Gly Glu Tyr Gln Tyr Trp Phe Asp Leu Asp Val
            340                 345                 350

Thr Asp His His Thr Asp Tyr Phe Ala Glu Phe
        355                 360
```

<210> SEQ ID NO 14
<211> LENGTH: 708
<212> TYPE: PRT
<213> ORGANISM: porcine epidemic diarrhea virus

<400> SEQUENCE: 14

```
Cys Ser Ala Asn Thr Asn Phe Arg Arg Phe Ser Lys Phe Asn Val
1               5                   10                  15

Gln Ala Pro Ala Val Val Leu Gly Gly Tyr Leu Pro Ile Gly Glu
            20                  25                  30

Asn Gln Gly Val Asn Ser Thr Trp Tyr Cys Ala Gly Gln His Pro Thr
        35                  40                  45

Ala Ser Gly Val His Gly Ile Phe Val Ser His Ile Arg Gly Gly His
    50                  55                  60

Gly Phe Glu Ile Gly Ile Ser Gln Glu Pro Phe Asp Pro Ser Gly Tyr
65                  70                  75                  80

Gln Leu Tyr Leu His Lys Ala Thr Asn Gly Asn Thr Asn Ala Thr Ala
                85                  90                  95

Arg Leu Arg Ile Cys Gln Phe Pro Ser Ile Lys Thr Leu Gly Pro Thr
                100                 105                 110

Ala Asn Asn Asp Val Thr Thr Gly Arg Asn Cys Leu Phe Asn Lys Ala
            115                 120                 125

Ile Pro Ala His Met Ser Glu His Ser Val Val Gly Ile Thr Trp Asp
        130                 135                 140

Asn Asp Arg Val Thr Val Phe Ser Asp Lys Ile Tyr Tyr Phe Tyr Phe
145                 150                 155                 160

Lys Asn Asp Trp Ser Arg Val Ala Thr Lys Cys Tyr Asn Ser Gly Gly
                165                 170                 175

Cys Ala Met Gln Tyr Val Tyr Glu Pro Thr Tyr Tyr Met Leu Asn Val
                180                 185                 190

Thr Ser Ala Gly Glu Asp Gly Ile Ser Tyr Gln Pro Cys Thr Ala Asn
                195                 200                 205

Cys Ile Gly Tyr Ala Ala Asn Val Phe Ala Thr Glu Pro Asn Gly His
            210                 215                 220

Ile Pro Glu Gly Phe Ser Phe Asn Asn Trp Phe Leu Leu Ser Asn Asp
225                 230                 235                 240

Ser Thr Leu Val His Gly Lys Val Val Ser Asn Gln Pro Leu Leu Val
                245                 250                 255

Asn Cys Leu Leu Ala Ile Pro Lys Ile Tyr Gly Leu Gly Gln Phe Phe
            260                 265                 270

Ser Phe Asn Gln Thr Ile Asp Gly Val Cys Asn Gly Ala Ala Val Gln
            275                 280                 285

Arg Ala Pro Glu Ala Leu Arg Phe Asn Ile Asn Asp Thr Ser Val Ile
    290                 295                 300

Leu Ala Glu Gly Ser Ile Val Leu His Thr Ala Leu Gly Thr Asn Phe
305                 310                 315                 320

Ser Phe Val Cys Ser Asn Ser Ser Asn Pro His Leu Ala Thr Phe Ala
            325                 330                 335

Ile Pro Leu Gly Ala Thr Gln Val Pro Tyr Tyr Cys Phe Phe Lys Val
            340                 345                 350

Asp Thr Tyr Asn Ser Thr Val Tyr Lys Phe Leu Ala Val Leu Pro Pro
            355                 360                 365

Thr Val Arg Glu Ile Val Ile Thr Lys Tyr Gly Asp Val Tyr Val Asn
        370                 375                 380

Gly Phe Gly Tyr Leu His Leu Gly Leu Leu Asp Ala Val Thr Ile Asn
385                 390                 395                 400

Phe Thr Gly His Gly Thr Asp Asp Val Ser Gly Phe Trp Thr Ile
                405                 410                 415
```

```
Ala Ser Thr Asn Phe Val Asp Ala Leu Ile Glu Val Gln Gly Thr Ala
                420                 425                 430

Ile Gln Arg Ile Leu Tyr Cys Asp Asp Pro Val Ser Gln Leu Lys Cys
            435                 440                 445

Ser Gln Val Ala Phe Asp Leu Asp Asp Gly Phe Tyr Pro Ile Ser Ser
        450                 455                 460

Arg Asn Leu Leu Ser His Glu Gln Pro Ile Ser Phe Val Thr Leu Pro
465                 470                 475                 480

Ser Phe Asn Asp His Ser Phe Val Asn Ile Thr Val Ser Ala Ser Phe
                485                 490                 495

Gly Gly His Ser Gly Ala Asn Leu Ile Ala Ser Asp Thr Thr Ile Asn
                500                 505                 510

Gly Phe Ser Ser Phe Cys Val Asp Thr Arg Gln Phe Thr Ile Ser Leu
            515                 520                 525

Phe Tyr Asn Val Thr Asn Ser Tyr Gly Tyr Val Ser Lys Ser Gln Asp
        530                 535                 540

Ser Asn Cys Pro Phe Thr Leu Gln Ser Val Asn Asp Tyr Leu Ser Phe
545                 550                 555                 560

Ser Lys Phe Cys Val Ser Thr Ser Leu Leu Ala Ser Ala Cys Thr Ile
                565                 570                 575

Asp Leu Phe Gly Tyr Pro Glu Phe Gly Ser Gly Val Lys Phe Thr Ser
                580                 585                 590

Leu Tyr Phe Gln Phe Thr Lys Gly Glu Leu Ile Thr Gly Thr Pro Lys
            595                 600                 605

Pro Leu Glu Gly Val Thr Asp Val Ser Phe Met Thr Leu Asp Val Cys
        610                 615                 620

Thr Lys Tyr Thr Ile Tyr Gly Phe Lys Gly Glu Gly Ile Ile Thr Leu
625                 630                 635                 640

Thr Asn Ser Ser Phe Leu Ala Gly Val Tyr Tyr Thr Ser Asp Ser Gly
                645                 650                 655

Gln Leu Leu Ala Phe Lys Asn Val Thr Ser Gly Ala Val Tyr Ser Val
                660                 665                 670

Thr Pro Cys Ser Phe Ser Glu Gln Ala Ala Tyr Val Asp Asp Asp Ile
            675                 680                 685

Val Gly Val Ile Ser Ser Leu Ser Ser Ser Thr Phe Asn Ser Thr Arg
        690                 695                 700

Glu Leu Pro Gly
705

<210> SEQ ID NO 15
<211> LENGTH: 170
<212> TYPE: PRT
<213> ORGANISM: Homo sapiens

<400> SEQUENCE: 15

Gln Ile Pro Gln Ala Pro Trp Pro Val Val Trp Ala Val Leu Gln Leu
1               5                   10                  15

Gly Trp Arg Pro Gly Trp Phe Leu Asp Ser Pro Asp Arg Pro Trp Asn
            20                  25                  30

Pro Pro Thr Phe Phe Pro Ala Leu Leu Val Val Thr Glu Gly Asp Asn
        35                  40                  45

Ala Thr Phe Thr Cys Ser Phe Ser Asn Thr Ser Glu Ser Phe Val Leu
    50                  55                  60

Asn Trp Tyr Arg Met Ser Pro Ser Asn Gln Thr Asp Lys Leu Ala Ala
65                  70                  75                  80
```

Phe Pro Glu Asp Arg Ser Gln Pro Gly Gln Asp Cys Arg Phe Arg Val
                85                  90                  95

Thr Gln Leu Pro Asn Gly Arg Asp Phe His Met Ser Val Val Arg Ala
            100                 105                 110

Arg Arg Asn Asp Ser Gly Thr Tyr Leu Cys Gly Ala Ile Ser Leu Ala
        115                 120                 125

Pro Lys Ala Gln Ile Lys Glu Ser Leu Arg Ala Glu Leu Arg Val Thr
    130                 135                 140

Glu Arg Arg Ala Glu Val Pro Thr Ala His Pro Ser Pro Ser Pro Arg
145                 150                 155                 160

Pro Ala Gly Gln Phe Gln Thr Asp Ile Tyr
                165                 170

<210> SEQ ID NO 16
<211> LENGTH: 569
<212> TYPE: PRT
<213> ORGANISM: Artificial Sequence
<220> FEATURE:
<223> OTHER INFORMATION: CSFV E2-gBac protein

<400> SEQUENCE: 16

Met Val Ser Ala Ile Val Leu Tyr Val Leu Leu Ala Ala Ala Ala His
1               5                   10                  15

Ser Ala Phe Ala Met Leu Arg Gly Gln Val Val Gln Gly Ile Ile Trp
            20                  25                  30

Leu Leu Leu Val Thr Gly Ala Gln Gly Arg Leu Ser Cys Lys Glu Asp
        35                  40                  45

His Arg Tyr Ala Ile Ser Ser Thr Asn Glu Ile Gly Pro Leu Gly Ala
    50                  55                  60

Glu Gly Leu Thr Thr Thr Trp Lys Glu Tyr Asn His Gly Leu Gln Leu
65                  70                  75                  80

Asp Asp Gly Thr Val Arg Ala Ile Cys Ile Ala Gly Ser Phe Lys Val
                85                  90                  95

Thr Ala Leu Asn Val Val Ser Arg Arg Tyr Leu Ala Ser Leu His Lys
            100                 105                 110

Arg Ala Leu Pro Thr Ser Val Thr Phe Glu Leu Leu Phe Asp Gly Thr
        115                 120                 125

Ser Pro Ala Ile Glu Glu Met Gly Asp Asp Phe Gly Phe Gly Leu Cys
    130                 135                 140

Pro Phe Asp Thr Thr Pro Val Val Lys Gly Lys Tyr Asn Thr Thr Leu
145                 150                 155                 160

Leu Asn Gly Ser Ala Phe Tyr Leu Val Cys Pro Ile Gly Trp Thr Gly
                165                 170                 175

Val Ile Glu Cys Thr Ala Val Ser Pro Thr Thr Leu Arg Thr Glu Val
            180                 185                 190

Val Lys Thr Phe Lys Arg Glu Lys Pro Phe Pro His Arg Val Asp Cys
        195                 200                 205

Val Thr Thr Ile Val Glu Lys Glu Asp Leu Phe Tyr Cys Lys Leu Gly
    210                 215                 220

Gly Asn Trp Thr Cys Val Lys Gly Asn Pro Val Thr Tyr Thr Gly Gly
225                 230                 235                 240

Gln Val Arg Gln Cys Arg Trp Cys Gly Phe Asp Phe Lys Glu Pro Asp
                245                 250                 255

Gly Leu Pro His Tyr Pro Ile Gly Lys Cys Ile Leu Thr Asn Glu Thr
            260                 265                 270

Gly Tyr Arg Val Val Asp Ser Pro Asp Cys Asn Arg Asp Gly Val Val
            275                 280                 285

Ile Ser Thr Glu Gly Glu His Glu Cys Leu Ile Gly Asn Thr Thr Val
        290                 295                 300

Lys Val His Ala Leu Asp Gly Arg Leu Ala Pro Met Pro Cys Arg Pro
305                 310                 315                 320

Lys Glu Ile Val Ser Ser Ala Gly Pro Val Arg Lys Thr Ser Cys Thr
                325                 330                 335

Phe Asn Tyr Thr Lys Thr Leu Arg Asn Lys Tyr Tyr Glu Pro Arg Asp
            340                 345                 350

Ser Tyr Phe Gln Gln Tyr Met Leu Lys Gly Tyr Gln Tyr Trp Phe
        355                 360                 365

Asp Leu Asp Val Thr Asp His His Thr Asp Tyr Phe Ala Glu Phe Ile
        370                 375                 380

Asn Lys Leu Asn Asn Met Leu His Asp Leu Ile Val Ser Val Ala Lys
385                 390                 395                 400

Val Asp Glu Arg Leu Ile Gly Asn Leu Met Asn Asn Ser Val Ser Ser
                405                 410                 415

Thr Phe Leu Ser Asp Asp Thr Phe Leu Leu Met Pro Cys Thr Asn Pro
            420                 425                 430

Pro Ala His Thr Ser Asn Cys Tyr Asn Asn Ser Ile Tyr Lys Glu Gly
            435                 440                 445

Arg Trp Val Ala Asn Thr Asp Ser Ser Gln Cys Ile Asp Phe Ser Asn
        450                 455                 460

Tyr Lys Glu Leu Ala Ile Asp Asp Val Glu Phe Trp Ile Pro Thr
465                 470                 475                 480

Ile Gly Asn Thr Thr Tyr His Asp Ser Trp Lys Asp Ala Ser Gly Trp
                485                 490                 495

Ser Phe Ile Ala Gln Gln Lys Ser Asn Leu Ile Thr Thr Met Glu Asn
            500                 505                 510

Thr Lys Phe Gly Gly Val Gly Thr Ser Leu Ser Asp Ile Thr Ser Met
        515                 520                 525

Ala Glu Gly Glu Leu Ala Ala Lys Leu Thr Ser Phe Met Phe Gly His
        530                 535                 540

Val Val Asn Phe Val Ile Ile Leu Ile Val Ile Leu Phe Leu Tyr Cys
545                 550                 555                 560

Met Ile Arg Asn Arg Asn Arg Gln Tyr
                565

<210> SEQ ID NO 17
<211> LENGTH: 914
<212> TYPE: PRT
<213> ORGANISM: Artificial Sequence
<220> FEATURE:
<223> OTHER INFORMATION: S1-gBac protein

<400> SEQUENCE: 17

Met Val Ser Ala Ile Val Leu Tyr Val Leu Leu Ala Ala Ala Ala His
1               5                   10                  15

Ser Ala Phe Ala Cys Ser Ala Asn Thr Asn Phe Arg Arg Phe Ser
            20                  25                  30

Lys Phe Asn Val Gln Ala Pro Ala Val Val Leu Gly Gly Tyr Leu
        35                  40                  45

Pro Ile Gly Glu Asn Gln Gly Val Asn Ser Thr Trp Tyr Cys Ala Gly
    50                  55                  60

```
Gln His Pro Thr Ala Ser Gly Val His Gly Ile Phe Val Ser His Ile
 65                  70                  75                  80

Arg Gly Gly His Gly Phe Glu Ile Gly Ile Ser Gln Glu Pro Phe Asp
                 85                  90                  95

Pro Ser Gly Tyr Gln Leu Tyr Leu His Lys Ala Thr Asn Gly Asn Thr
            100                 105                 110

Asn Ala Thr Ala Arg Leu Arg Ile Cys Gln Phe Pro Ser Ile Lys Thr
        115                 120                 125

Leu Gly Pro Thr Ala Asn Asn Asp Val Thr Thr Gly Arg Asn Cys Leu
130                 135                 140

Phe Asn Lys Ala Ile Pro Ala His Met Ser Glu His Ser Val Val Gly
145                 150                 155                 160

Ile Thr Trp Asp Asn Asp Arg Val Thr Val Phe Ser Asp Lys Ile Tyr
                165                 170                 175

Tyr Phe Tyr Phe Lys Asn Asp Trp Ser Arg Val Ala Thr Lys Cys Tyr
            180                 185                 190

Asn Ser Gly Gly Cys Ala Met Gln Tyr Val Tyr Glu Pro Thr Tyr Tyr
        195                 200                 205

Met Leu Asn Val Thr Ser Ala Gly Glu Asp Gly Ile Ser Tyr Gln Pro
210                 215                 220

Cys Thr Ala Asn Cys Ile Gly Tyr Ala Ala Asn Val Phe Ala Thr Glu
225                 230                 235                 240

Pro Asn Gly His Ile Pro Glu Gly Phe Ser Phe Asn Asn Trp Phe Leu
                245                 250                 255

Leu Ser Asn Asp Ser Thr Leu Val His Gly Lys Val Val Ser Asn Gln
            260                 265                 270

Pro Leu Leu Val Asn Cys Leu Leu Ala Ile Pro Lys Ile Tyr Gly Leu
        275                 280                 285

Gly Gln Phe Phe Ser Phe Asn Gln Thr Ile Asp Gly Val Cys Asn Gly
290                 295                 300

Ala Ala Val Gln Arg Ala Pro Glu Ala Leu Arg Phe Asn Ile Asn Asp
305                 310                 315                 320

Thr Ser Val Ile Leu Ala Glu Gly Ser Ile Val Leu His Thr Ala Leu
                325                 330                 335

Gly Thr Asn Phe Ser Phe Val Cys Ser Asn Ser Ser Asn Pro His Leu
            340                 345                 350

Ala Thr Phe Ala Ile Pro Leu Gly Ala Thr Gln Val Pro Tyr Tyr Cys
        355                 360                 365

Phe Phe Lys Val Asp Thr Tyr Asn Ser Thr Val Tyr Lys Phe Leu Ala
370                 375                 380

Val Leu Pro Pro Thr Val Arg Glu Ile Val Ile Thr Lys Tyr Gly Asp
385                 390                 395                 400

Val Tyr Val Asn Gly Phe Gly Tyr Leu His Leu Gly Leu Leu Asp Ala
                405                 410                 415

Val Thr Ile Asn Phe Thr Gly His Gly Thr Asp Asp Asp Val Ser Gly
            420                 425                 430

Phe Trp Thr Ile Ala Ser Thr Asn Phe Val Asp Ala Leu Ile Glu Val
        435                 440                 445

Gln Gly Thr Ala Ile Gln Arg Ile Leu Tyr Cys Asp Asp Pro Val Ser
450                 455                 460

Gln Leu Lys Cys Ser Gln Val Ala Phe Asp Leu Asp Asp Gly Phe Tyr
465                 470                 475                 480
```

```
Pro Ile Ser Ser Arg Asn Leu Leu Ser His Glu Gln Pro Ile Ser Phe
                485                 490                 495
Val Thr Leu Pro Ser Phe Asn Asp His Ser Phe Val Asn Ile Thr Val
            500                 505                 510
Ser Ala Ser Phe Gly Gly His Ser Gly Ala Asn Leu Ile Ala Ser Asp
        515                 520                 525
Thr Thr Ile Asn Gly Phe Ser Ser Phe Cys Val Asp Thr Arg Gln Phe
    530                 535                 540
Thr Ile Ser Leu Phe Tyr Asn Val Thr Asn Ser Tyr Gly Tyr Val Ser
545                 550                 555                 560
Lys Ser Gln Asp Ser Asn Cys Pro Phe Thr Leu Gln Ser Val Asn Asp
                565                 570                 575
Tyr Leu Ser Phe Ser Lys Phe Cys Val Ser Thr Ser Leu Leu Ala Ser
            580                 585                 590
Ala Cys Thr Ile Asp Leu Phe Gly Tyr Pro Glu Phe Gly Ser Gly Val
        595                 600                 605
Lys Phe Thr Ser Leu Tyr Phe Gln Phe Thr Lys Gly Glu Leu Ile Thr
    610                 615                 620
Gly Thr Pro Lys Pro Leu Glu Gly Val Thr Asp Val Ser Phe Met Thr
625                 630                 635                 640
Leu Asp Val Cys Thr Lys Tyr Thr Ile Tyr Gly Phe Lys Gly Glu Gly
                645                 650                 655
Ile Ile Thr Leu Thr Asn Ser Ser Phe Leu Ala Gly Val Tyr Tyr Thr
            660                 665                 670
Ser Asp Ser Gly Gln Leu Leu Ala Phe Lys Asn Val Thr Ser Gly Ala
        675                 680                 685
Val Tyr Ser Val Thr Pro Cys Ser Phe Ser Glu Gln Ala Ala Tyr Val
    690                 695                 700
Asp Asp Asp Ile Val Gly Val Ile Ser Ser Leu Ser Ser Ser Thr Phe
705                 710                 715                 720
Asn Ser Thr Arg Glu Leu Pro Gly Ile Asn Lys Leu Asn Asn Met Leu
                725                 730                 735
His Asp Leu Ile Val Ser Val Ala Lys Val Asp Glu Arg Leu Ile Gly
            740                 745                 750
Asn Leu Met Asn Asn Ser Val Ser Ser Thr Phe Leu Ser Asp Asp Thr
        755                 760                 765
Phe Leu Leu Met Pro Cys Thr Asn Pro Pro Ala His Thr Ser Asn Cys
    770                 775                 780
Tyr Asn Asn Ser Ile Tyr Lys Glu Gly Arg Trp Val Ala Asn Thr Asp
785                 790                 795                 800
Ser Ser Gln Cys Ile Asp Phe Ser Asn Tyr Lys Glu Leu Ala Ile Asp
                805                 810                 815
Asp Asp Val Glu Phe Trp Ile Pro Thr Ile Gly Asn Thr Thr Tyr His
            820                 825                 830
Asp Ser Trp Lys Asp Ala Ser Gly Trp Ser Phe Ile Ala Gln Gln Lys
        835                 840                 845
Ser Asn Leu Ile Thr Thr Met Glu Asn Thr Lys Phe Gly Gly Val Gly
    850                 855                 860
Thr Ser Leu Ser Asp Ile Thr Ser Met Ala Glu Gly Glu Leu Ala Ala
865                 870                 875                 880
Lys Leu Thr Ser Phe Met Phe Gly His Val Val Asn Phe Val Ile Ile
                885                 890                 895
Leu Ile Val Ile Leu Phe Leu Tyr Cys Met Ile Arg Asn Arg Asn Arg
```

-continued

```
                    900             905             910

Gln Tyr

<210> SEQ ID NO 18
<211> LENGTH: 376
<212> TYPE: PRT
<213> ORGANISM: Artificial Sequence
<220> FEATURE:
<223> OTHER INFORMATION: hPD1-gBac protein

<400> SEQUENCE: 18

Met Val Ser Ala Ile Val Leu Tyr Val Leu Leu Ala Ala Ala Ala His
1               5                   10                  15

Ser Ala Phe Ala Gln Ile Pro Gln Ala Pro Trp Pro Val Val Trp Ala
            20                  25                  30

Val Leu Gln Leu Gly Trp Arg Pro Gly Trp Phe Leu Asp Ser Pro Asp
        35                  40                  45

Arg Pro Trp Asn Pro Pro Thr Phe Phe Pro Ala Leu Leu Val Val Thr
    50                  55                  60

Glu Gly Asp Asn Ala Thr Phe Thr Cys Ser Phe Ser Asn Thr Ser Glu
65                  70                  75                  80

Ser Phe Val Leu Asn Trp Tyr Arg Met Ser Pro Ser Asn Gln Thr Asp
                85                  90                  95

Lys Leu Ala Ala Phe Pro Glu Asp Arg Ser Gln Pro Gly Gln Asp Cys
            100                 105                 110

Arg Phe Arg Val Thr Gln Leu Pro Asn Gly Arg Asp Phe His Met Ser
        115                 120                 125

Val Val Arg Ala Arg Arg Asn Asp Ser Gly Thr Tyr Leu Cys Gly Ala
    130                 135                 140

Ile Ser Leu Ala Pro Lys Ala Gln Ile Lys Glu Ser Leu Arg Ala Glu
145                 150                 155                 160

Leu Arg Val Thr Glu Arg Arg Ala Glu Val Pro Thr Ala His Pro Ser
                165                 170                 175

Pro Ser Pro Arg Pro Ala Gly Gln Phe Gln Thr Asp Ile Tyr Ile Asn
            180                 185                 190

Lys Leu Asn Asn Met Leu His Asp Leu Ile Val Ser Val Ala Lys Val
        195                 200                 205

Asp Glu Arg Leu Ile Gly Asn Leu Met Asn Asn Ser Val Ser Ser Thr
    210                 215                 220

Phe Leu Ser Asp Asp Thr Phe Leu Leu Met Pro Cys Thr Asn Pro Pro
225                 230                 235                 240

Ala His Thr Ser Asn Cys Tyr Asn Asn Ser Ile Tyr Lys Glu Gly Arg
                245                 250                 255

Trp Val Ala Asn Thr Asp Ser Ser Gln Cys Ile Asp Phe Ser Asn Tyr
            260                 265                 270

Lys Glu Leu Ala Ile Asp Asp Val Glu Phe Trp Ile Pro Thr Ile
        275                 280                 285

Gly Asn Thr Thr Tyr His Asp Ser Trp Lys Asp Ala Ser Gly Trp Ser
    290                 295                 300

Phe Ile Ala Gln Gln Lys Ser Asn Leu Ile Thr Thr Met Glu Asn Thr
305                 310                 315                 320

Lys Phe Gly Gly Val Gly Thr Ser Leu Ser Asp Ile Thr Ser Met Ala
                325                 330                 335

Glu Gly Glu Leu Ala Ala Lys Leu Thr Ser Phe Met Phe Gly His Val
            340                 345                 350
```

```
Val Asn Phe Val Ile Ile Leu Ile Val Ile Leu Phe Leu Tyr Cys Met
        355                 360                 365

Ile Arg Asn Arg Asn Arg Gln Tyr
    370                 375

<210> SEQ ID NO 19
<211> LENGTH: 15
<212> TYPE: DNA
<213> ORGANISM: Artificial Sequence
<220> FEATURE:
<223> OTHER INFORMATION: SP forward primer

<400> SEQUENCE: 19
gagctcatgg taagc                                                       15

<210> SEQ ID NO 20
<211> LENGTH: 12
<212> TYPE: DNA
<213> ORGANISM: Artificial Sequence
<220> FEATURE:
<223> OTHER INFORMATION: SP reverse pirmer

<400> SEQUENCE: 20
aggcagaatg cg                                                          12

<210> SEQ ID NO 21
<211> LENGTH: 13
<212> TYPE: DNA
<213> ORGANISM: Artificial Sequence
<220> FEATURE:
<223> OTHER INFORMATION: gp64 forward primer

<400> SEQUENCE: 21
gcgtgtctgc tca                                                         13

<210> SEQ ID NO 22
<211> LENGTH: 13
<212> TYPE: DNA
<213> ORGANISM: Artificial Sequence
<220> FEATURE:
<223> OTHER INFORMATION: gp64 reverse pirmer

<400> SEQUENCE: 22
ttaatattgt cta                                                         13

<210> SEQ ID NO 23
<211> LENGTH: 13
<212> TYPE: DNA
<213> ORGANISM: Artificial Sequence
<220> FEATURE:
<223> OTHER INFORMATION: gp64 forward pirmer

<400> SEQUENCE: 23
atcaacaagc taa                                                         13

<210> SEQ ID NO 24
<211> LENGTH: 13
<212> TYPE: DNA
<213> ORGANISM: Artificial Sequence
<220> FEATURE:
<223> OTHER INFORMATION: gp64 reverse pirmer

<400> SEQUENCE: 24
ttaatattgt cta                                                         13
```